United States Patent [19]

Bull et al.

[11] 4,073,621
[45] Feb. 14, 1978

[54] READER RECORDER FOR TOXIC GAS CONCENTRATION TAPES

[75] Inventors: Rame Bull, Mount Prospect; Byron A. Denenberg, Northfield; Djorde R. Popovic, Chicago, all of Ill.

[73] Assignee: MDA Scientific, Inc., Park Ridge, Ill.

[21] Appl. No.: 661,134

[22] Filed: Feb. 25, 1976

[51] Int. Cl.² ........................ G01D 9/38; G01N 21/30
[52] U.S. Cl. ........................... 23/254 E; 23/255 E; 23/253 TP; 346/33 A
[58] Field of Search ............ 23/253 R, 254 R, 254 E, 23/232 R, 232 E, 255 R, 255 E, 253 TP; 235/151.35; 346/33 A; 73/23

[56] References Cited

U.S. PATENT DOCUMENTS

| 2,232,622 | 2/1941 | Moses et al. | 23/255 R |
| 2,551,281 | 5/1951 | Moses et al. | 23/255 R |
| 2,800,397 | 7/1957 | Offutt et al. | 23/255 R |
| 2,895,807 | 7/1959 | Sorg et al. | 23/255 R |
| 3,460,153 | 8/1969 | White | 23/254 X |

OTHER PUBLICATIONS

"Monitor" Newsletter of MDA Scientific, Inc., Dec. 1974.

*Primary Examiner*—R.E. Serwin
*Attorney, Agent, or Firm*—McDougall, Hersh & Scott

[57] ABSTRACT

A reader recorder which will plot a concentration versus time graph based on stain intensity of a gas sensitive tape. Simultaneously, the device will integrate the area under the curve to obtain the total dosage for the period of time covered by the graph. By means of a common drive system for the recorder and the tape drive a meaningful relationship between displacement on the tape and position on the graph is obtained yielding information on the exact time of occurrence of events of interest.

9 Claims, 11 Drawing Figures

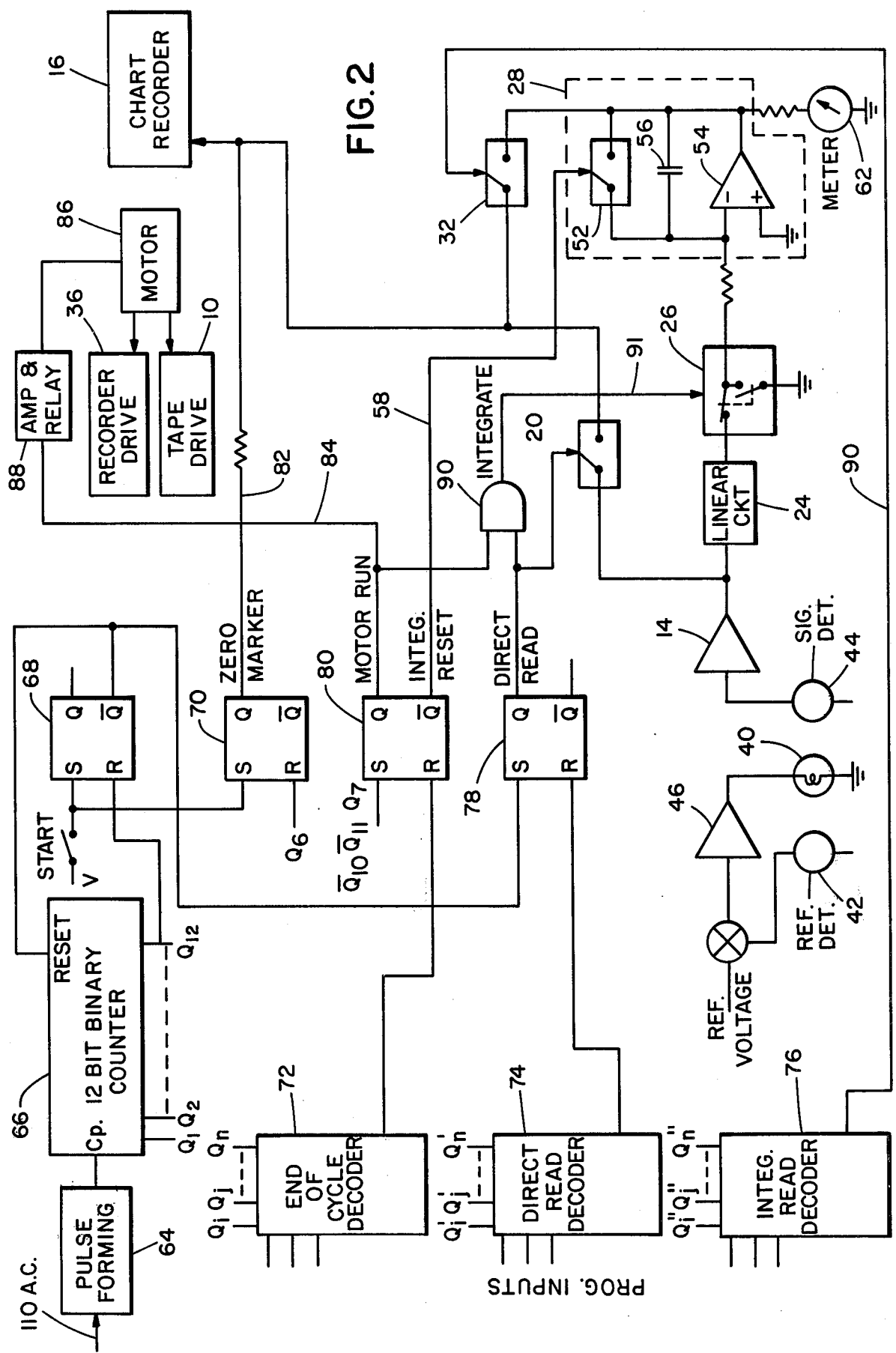

READER RECORDER FOR TOXIC GAS CONCENTRATION TAPES

BACKGROUND OF THE INVENTION

This invention relates to the field of detection and monitoring of vapors and gases. In particular, it relates to the field of detection and monitoring of toxic gases and vapors in industrial environments. A wide variety of hazardous substances are utilized in industrial manufacturing and processing, some of which give off gases and vapors of the toxic variety in ambient air in areas both internal and external to the industrial facility.

In order to protect workers from the effects of exposure to these hazardous substances, and to study their acute and chronic effects, it is useful to monitor the air which such workers breathe during the periods in which they are in the vicinity of these hazardous substances in order to determine and document the contaminant concentrations.

An example of the type of industrial applications which require toxic gas and vapor monitoring is the manufacture of polyurethane foam. In the manufacture of polyurethane foam, toluene di-isocyante (TDI) is utilized. Workers who inhale excessive TDI concentrations will experience respiratory irritation and sensitization. Serious adverse effects to such exposure are only now coming to the attention of medical safety researchers. The literature indicates that these effects occur at low exposure levels.

Other toxic gases or vapors present similar safety problems including phosgene, chlorine, hydrogen sulfide, nitrogen dioxide, vinyl chloride and sulfur dioxide.

Known sampling techniques for detecting levels of toxic gases to which workers are exposed have not been satisfactory. A particular problem is that high peaks of brief exposure do not show up. There is evidence to suggest that high excursions of short duration may be a significant factor in assessing the effect of the toxic substance on the worker.

A recent development in the field is a portable miniaturized monitor which exposes a roll of gas sensitive chemically treated tape in the breathing zone of a worker. This device is the subject of a co-pending patent application Ser. No. 567,379 filed Apr. 11, 1975, by the present assignee and hereby incorporated by reference. Upon exposure, a stain develops upon a portion of the tape which is later read on a readout device such as presently disclosed. Since reading of the tape occurs after exposure, the monitor includes means to prevent contamination of adjacent layers of tape. After a worker's shift is ended, the exposed tape is removed from the monitor and placed into the reader recorder to produce a permanent, graphic display of concentration versus time and total dose values. From this information, a time-weighted average exposure level as well as excursions above a predetermined maximum ceiling can be determined.

Reference is made to the U.S. Department of Labor, Occupational Health & Safety Administration publication, *Job Safety & Health,* Volume II, No. 11, for additional background on the subject of monitoring TDI and other toxic gases.

SUMMARY OF THE INVENTION

The present invention produces a chart record of gas concentration versus time and total 8 hour dose as determined from tape exposed in a gas monitor. The intensity of the stain on the tape is related to the concentration of gas.

The exposed tape is passed through the optical reader portion of the invention and measured stain intensity is recorded versus time to provide an easily read, permanent record of gas concentration versus time. While the concentration versus time function is being produced the invention also integrates the concentration as a function of time to determine the total dose for the given period, say 8 hours. This total dose is recorded on the chart in bar graph format at the end of the concentration versus time plot.

OBJECTS OF THE INVENTION

It is an object of the invention to provide a reader recorder capable of reading a gas sensitive tape to produce a plot of gas concentration versus time.

Another object of the invention is to provide a reader recorder which is capable of producing a graph of concentration versus time and of integrating the area under such graph to obtain the total dosage for the indicated time period.

It is another object of the invention to provide a reader recorder which utilizes a drive system in which the tape drive and the recorder drive are maintained in synchronism so that the time of occurrence of events of interest can be identified.

A further object of the invention is to provide a means for rapidly producing a read out of concentration versus time for a toxic gas.

Other objects and advantages of the invention will be apparent from the remaining portion of the specification.

BRIEF DESCRIPTION OF THE DRAWINGS

FIG. 1A is a segment of exposed tape read by the invention.

FIG. 2 is a partial schematic circuit diagram of the invention.

DETAILED DESCRIPTION

Figure 1:
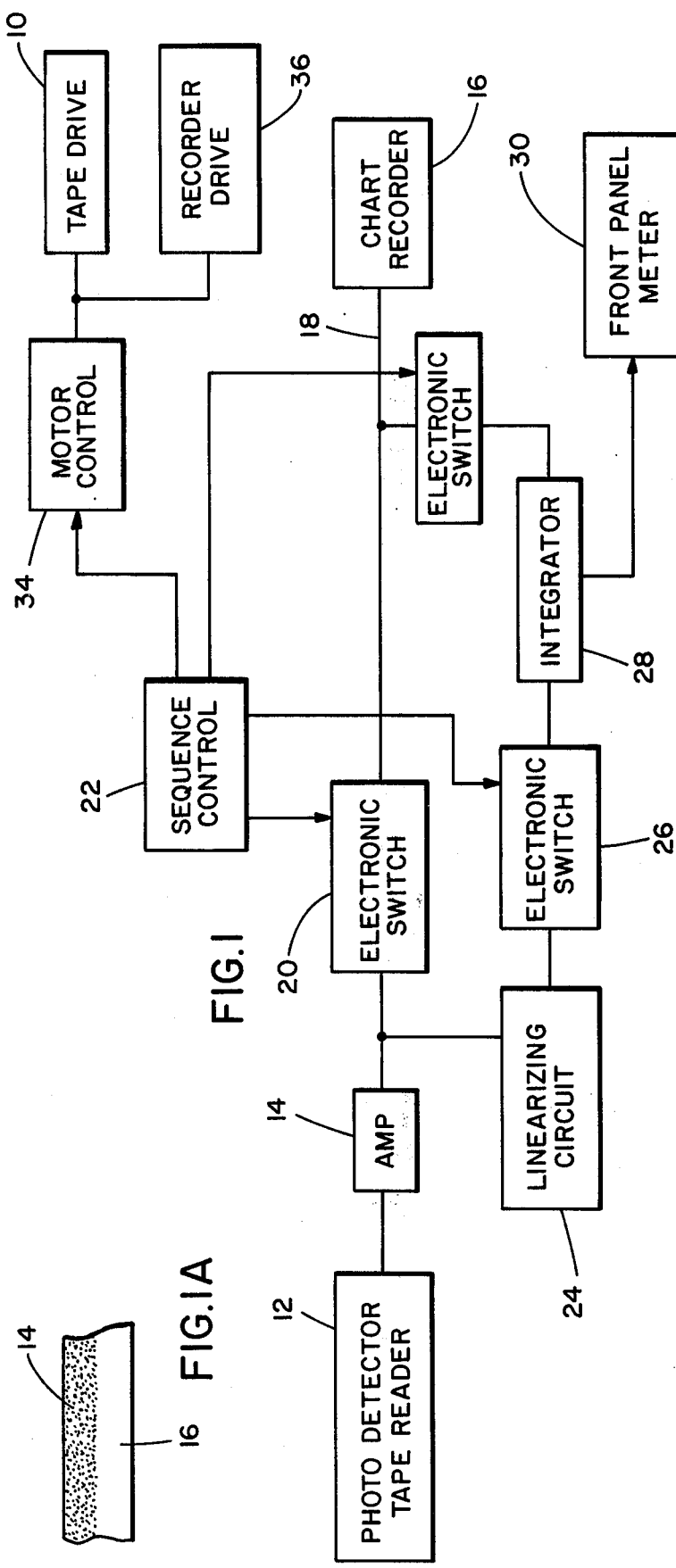
FIG. 1 is a block diagram of the reader recorder according to the invention.

Referring to FIG. 1, a block diagram of the invention is illustrated. An exposed tape, sensitive to a toxic gas, is produced in the manner described in the above referenced copending patent application and is placed in a tape reader section which includes a tape drive 10 for moving the tape past a photocell optical section 12. The photocell optical reader 12 utilizes the technique of applying a source of light of known intensity to the tape and measuring the light reflected from the tape as an indication of stain intensity. In order to maintain the light at the proper intensity, a reference photocell is employed for measuring the reflected light from an unstained portion of the tape.

In FIG. 1A a section of tape is illustrated in which the upper half 14 is stained from exposure to the gas being monitored while the lower half 16 is unstained and serves as the reference portion during reading of the tape. The output from the photocell optical reader 12 is provided to an amplifier 14 to increase the signal level for use throughout the balance of the circuit. From amplifier 14 the photocell signal which is a direct function of the stain intensity of the tape is provided to a chart recorder 16 via line 18 whenever an electronic switch 20 is operated by a sequence control circuit 22.

The output of the amplifier 14 is also provided to a linearizing circuit 24. The linearizing circuit is described below. Briefly, however, its purpose is to produce a linear relationship between stain intensity and the output voltage from amplifier 14 so that a straightforward integration of the area under a stain intensity versus time curve may be performed. The output of the linerizing circuit 24 is connected via an electronic switch 26 to an integrator 28. The output of the integrator is provided to a front panel meter 30 so that the value may be continuously monitored during the operation of the invention. By means of an electronic switch 32 the output of the integrator is also provided to the chart recorder 16 so that at the end of a tape segment the total dosage may be printed out directly by the chart recorder. When switch 32 is utilized to connect the integrator 28 to the chart recorder, switch 20 is opened disconnecting the direct signal.

The sequence control 22 in addition to correctly operating the electronic switches 20, 26 and 32 also includes necessary timing logic for operating the mechanical sections of the invention. Specifically, timing logic is provided for turning the drive motor on and off via motor control 34. A primary advantage of the present invention is a directly proportional relationship between distance on the tape being read and distance on the chart or graph being produced by the chart recorder. This is preferably achieved by providing a single motor to drive both the tape and the chart. Thus, there is a known relationship between the tape drive and the chart recorder drive 36. Desirably, this relationship may be some whole integer ratio, such as one to one or two to one so that a given segment of tape which, for example, may represent an eight hour shift, will repeatedly produce a given length of output from the chart recorder. That output may then be characterized as the graph of an 8 hour shift of exposure to a toxic gas. Similarly, under these circumstances, the integral of the area under such a curve is representative of the total dosage over that period of time. From such information the time weighted average can be rapidly calculated by dividing the total dose for the given period by the number of hours in the period.

Figure 4:
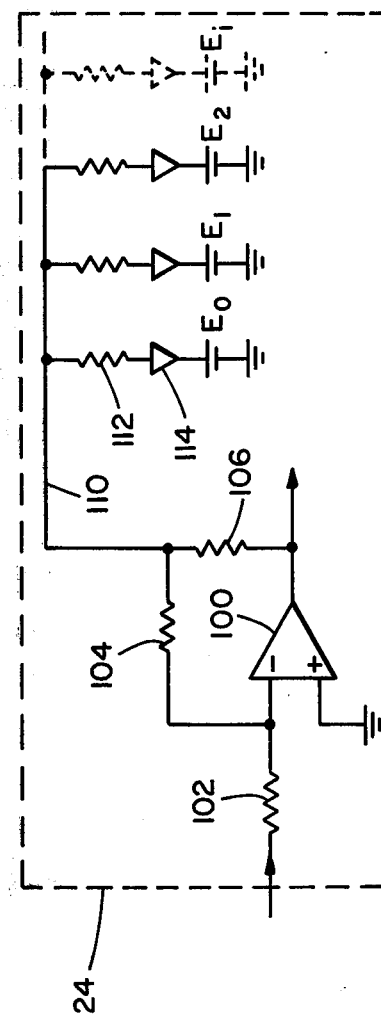
FIG. 4 is a schematic of the linearizing section of the circuit.
Figure 3:
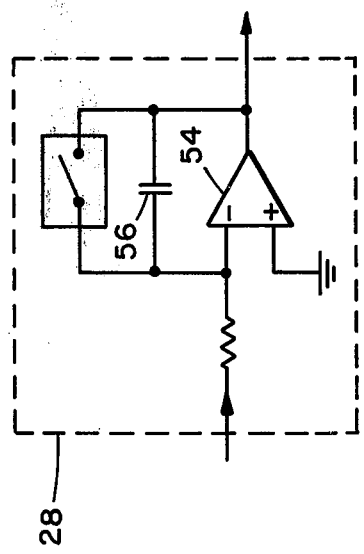
FIG. 3 is a schematic of the integrator section of the invention.

Referring now to FIGS. 2, 3 and 4, the schematic circuitry for the present invention is disclosed. The photocell optical reader 12 includes an incandescent light source 40 and two matched photoelectric detectors 42 and 44. Detector 42 is a reference detector positioned to measure reflected light from the unexposed portion of the tape. The output of the reference detector is fed to a reference amplifier 46 which compares the output against a reference level. If the output of reference detector 42 falls below the reference level, a signal is generated by amplifier 46 for increasing the voltage applied to incandescent light source 40. The opposite action occurs if the reference detector exceeds the reference value, and the light source voltage is decreased. In this manner a constant reference level is provided against which the signal detector output 44 can be measured so that the stain intensity detected by signal detector 44 on the exposed portion of the gas sensitive tape is truly indicative of stain intensity.

The output from the signal detector 44 is fed to the signal amplifier 14. The output of the amplifier is supplied to the chart recorder 16 via an electronic switch 20 and line 18. As schematically indicated, electronic switch 20 is controlled by the sequential control portion of the circuit and when activated completes a circuit to the chart recorder. Switch 20 can be any of a large number of available solid state switches such as switch 2N5458. The switch is operated by activating line 50 from the sequence control portion of the circuit.

As indicated in FIG. 2, the amplified output from amplifier 14 is also applied to a linearizing circuit 24 and then through a ganged switch 26 to the integrator 28. The integrator 28 includes an electronic switch 52 for resetting the integrator.

The integrator 28 is of classical construction including an operational amplifier 54 and a feedback capacitor 56. The switch 52 is connected across the feedback capacitor 56 and when actuated discharges the capacitor thereby resetting the integrator. Switch 52 is operated from line 58 which is controlled by the sequence control circuitry. Connected to the output of the operational amplifier 54 via resistor 60 is a direct reading meter 62 for indicating the output of the integrator. The integrator output is also connected to the recorder via switch 32.

Referring now to the sequence control circuit, the circuit derives its timing pulses from the line voltage which in most cases is 110 volts 60 cycles. A pulse forming network 64 provides pulses to drive a twelve bit binary counter 66. The outputs of the binary counter are indicated as Q1 through Q12 and these outputs are utilized throughout the remaining portion of the sequence control circuit for accurately gating the various functions. The binary counter is reset until a push button is manually actuated initiating system operation. The push button is indicated in FIG. 2 as the signal start which is provided to the set inputs of R-S flipflops 68 and 70. The start signal sets those flipflops and permits the binary counter 66 to initiate its counting sequence. As the counter cycles through its sequence, the outputs Q1 through 12 will provide various code combinations which are utilized by the decoders 72, 74 and 76 as well as the flipflops 68, 70, 78 and 80.

Flipflop 68 is set for the entire operating cycle and is not reset until the Q12 output of binary counter 66 goes high. This resets flipflop 68 and again maintains the binary counter 66 in its reset condition.

Figure 8:
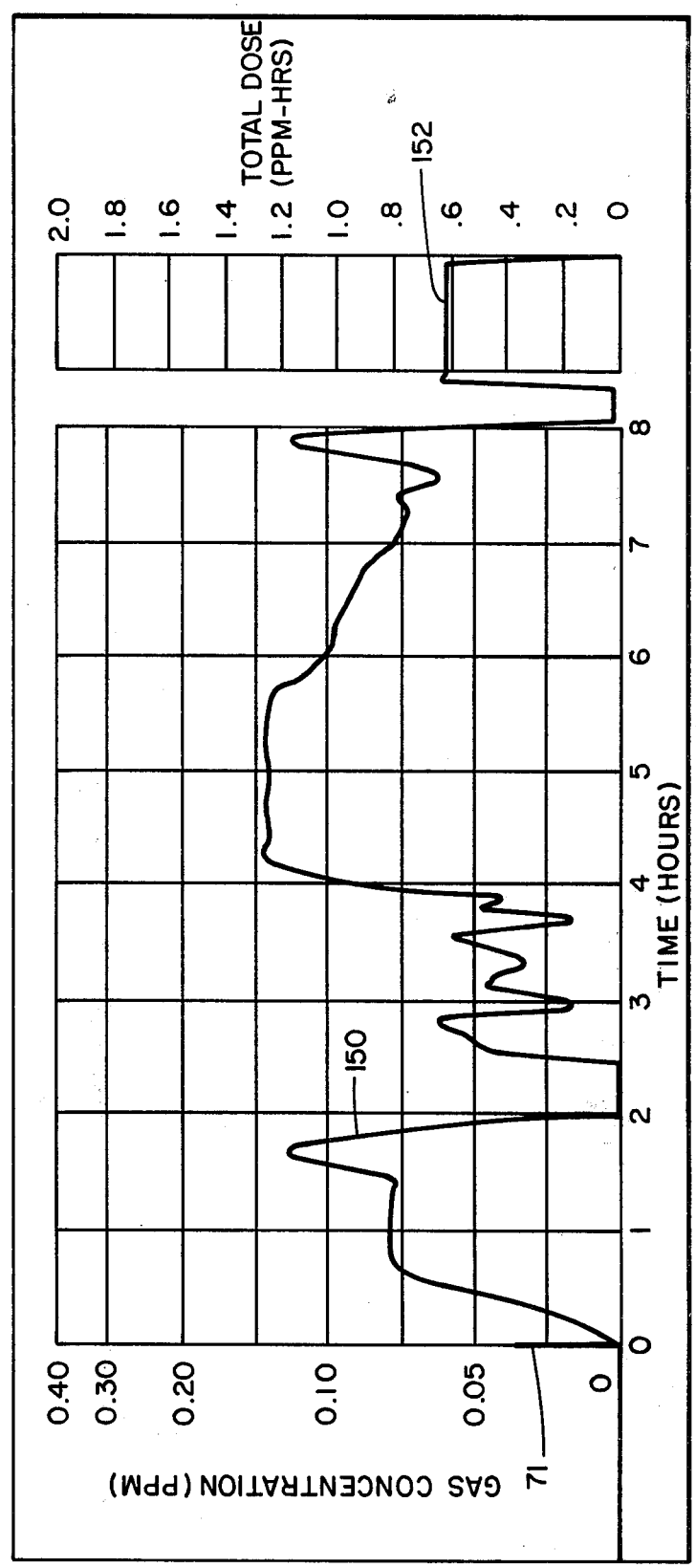
FIG. 8 is an illustration of a typical time versus concentration graph and of the bar chart print out of total dosage as produced by the present invention.

Flipflop 70 controls operation of the zero marker function. The zero marker is a short vertical pulse applied to the recorder before each run. It indicates the beginning of a recording run. The zero marker pulse is applied to the recorder when flipflop 70 is set and terminates when the binary counter reaches the value of Q6 resetting flipflop 70. The Q output of flipflop 70 is provided via line 82 to the chart recorder for the purpose of deflecting the recorder pen for producing the zero marker 71 as illustrated in FIG. 8.

Setting flipflop 80 turns on the motor to drive the chart recorder and the tape reader. Flipflop 80 is set when counter 66 reaches Q7 for the first time. This is referred to hereafter as the motor run signal and is produced on line 84 and supplied to the motor 86 via an amplifier and relay 88. In turn the motor drives the recorder drive 36 and the tape drive 10 as schematically indicated. The motor run signal is also provided to AND gate 90 for a purpose to be described.

Flipflop 78 is set when the power is first turned on and each time the 12 bit binary counter 66 reaches the end of its cycle. Thus, before the beginning of each new cycle, flipflop 78 is already set so that the direct read output on line 50 closes switch 20. This provides the output from the signal detector 44 to the recorder 16. In this manner the recorder can be calibrated and adjusted and the zero marker can be drawn on the chart paper. The direct read signal from flipflop 78 is also provided as the second input to AND gate 90. The output of AND gate 90, therefore, indicates a condition when the motor is running and the output from the signal detector 44 is being provided to the recorder. Under these circumstances, switch 26 is actuated via line 91. Switch 26 is the integrator input clamp and connects the integrator input to the output of the linearizing circuit 24 or to ground. In the absence of a signal from gate 90, the input to the integrator is clamped to ground. Thus, integration takes place only while the direct signal is applied to the recorder and the motor is running. The switch 26 may be a commercially available electronic switch, such as, a type MC14816. Flipflop 80 controls the resetting of the integrator via line 58 and switch 52. It will be apparent from the connection of line 58 to the Q output that the integrator is reset when the motor is off.

Subsequent operation of flipflops 78 and 80 is controlled by the decoders 74 and 72, respectively, which detect a preselected code from the binary counter 66. The decoders are of the commercially available type as, for example, MC14512. Such decoders recognize a specific input combination and produce an output signal which is applied to the reset input of the flip-flops. Thus, when the appropriate code is detected by the decoders, the flipflops 78 and 80 are reset. In the case of flipflop 78 and decoder 74, when the binary counter produces the necessary combination indicative of sufficient time to complete reading of a tape, an output is produced from the decoder resetting flipflop 78. This disables AND gate 90 and electronic switch 20 thereby disconnecting the chart recorder 16 from the signal detector 44. It also clamps the integrator 28 to ground rather than to the output of the linearizing circuit 24 via line 91. It should be noted that the integrator is not reset at this time but its input is maintained at ground to prevent any further integration from stray signals.

A short time after decoder 74 resets flipflop 78, decoder 76 produces an output on line 90 to operate electronic switch 32. This permits the output of the integrator 28 to be applied to the chart recorder 16. Since decoder 72 has not reset flipflop 80 the motor continues to run. Thus, the integrator output is printed by the chart recorder 16 onto the graph paper moving therethrough. This produces a bar graph 152 which is equal to the integral of the area under the curve of the direct reading wave form. A short time later the decoder 76 output disables switch 32.

Finally, the decoder 72 resets flipflop 80 which stops the motor and resets the integrator for the next cycle. When the counter 66 produces a Q12 output, flipflop 68 is reset thereby setting flipflop 78. The binary counter, however, stays reset until the start signal is received from the start push button.

Referring now to FIGS. 3 and 4, the integrator and linearizing circuit are shown in greater detail. As indicated previously, it is highly desirable to calculate the total dose for a given time interval. The total dose D for a time T is $$D = \int_o^T F\, dt$$

where $F$ is a function relating the detector signal to the actual gas concentration. In order to perform this integration in a straightforward manner, it is necessary that $F$ be an easily handled, i.e., linear function. That is, if $F = KC$ where K is a constant and C is the concentration, then the total dose is equal to $$D = K \int_o^T c\, dt.$$

Such a linear relationship permits integration to be done in the classical manner by a circuit such as shown in FIG. 3.

Figure 5A:
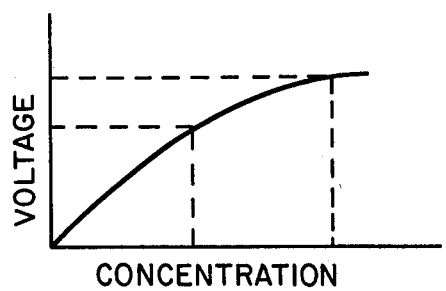
FIGS. 5A, B and C are a set of curves illustrating the purpose and function of the linearizing circuit of FIG. 4.

The relationship between reflected light from the photocell section of the reader recorder and gas concentration is for a number of toxic gases as, for example, TDI, a non-linear function. Specifically, the relationship between reflected light and TDI concentration is essentially logarithmic. This relationship is illustrated in FIG. 5A wherein the ordinate is a plot of gas concentration and the abscissa is a plot of output voltage from the amplifier 14. In order to employ an integrator of the form illustrated in FIG. 3, it is necessary that the relationship between gas concentration and output voltage be altered to provide a linear relationship. For that purpose the linearizing circuit of FIG. 4 is provided. The output voltage from the amplifier 14 is provided as an input to the linearizing circuit 24. The linearizing circuit alters the input signal by applying a voltage which is of the opposite logarithmatic slope. The latter is illustrated in FIG. 5B wherein the ordinate represents the input voltage from amplifier 14 and the abscissa represents the output voltage from the linearizing circuit.

Figure 5B:
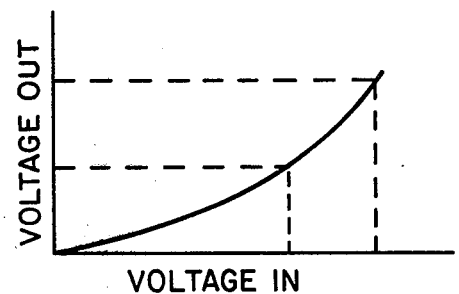
Figure 5C:
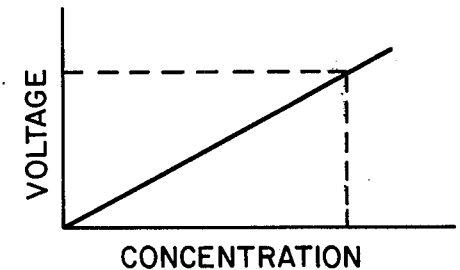

If the linearizing circuit is properly set, the resultant of applying the logarithmatic signal of FIG. 5A to the linearizing circuit of FIG. 5B will be to produce an output as illustrated in FIG. 5C. That is, for a given concentration of toxic gas the output voltage from the linearizing circuit will have the relationship indicated in FIG. 5C. This is a linear relationship of voltage to gas concentration.

FIG. 4 schematically illustrates the circuit used to produce this result. The linearizing circuit includes an operational amplifier 100, input resistor 102, feedback resistors 104 and 106. The voltage gain, G, from a network such as thus far described is approximately $G = R_{102}/(R_{104} + R_{106})$. The gain is proportional to the amount of feedback in the circuit. By means of line 110 a number of parallel resistor diode elements are added to the feedback network. Each parallel element includes a resistor, a diode and a voltage source. For example, resistor 112, diode 114 and voltage source E0. The values of the resistors and the voltage sources differ in the remaining elements.

With the diode network connected to the midpoint of resistors 104 and 106 the amount of feedback in the operational amplifier circuit is reduced and the gain increased as the diodes begin to conduct. By setting the voltage threshold at which each diode begins to conduct the gain can be made to change as an arbitrary function of the input voltage. The curve can be shaped as desired by choosing the values of the voltage sources E0, E1, etc., and the value of resistors in series with the diodes.

The linearizing circuit of FIG. 4 may thus be thought of as a variable gain amplifier such that the output changes with the input voltage. This circuit can produce the curve of FIG. 5B which curve is the reciprocal or inverse of the curve of FIG. 5A thereby producing the linear relationship of FIG. 5C as necessary for proper operation of the integrator 28.

Figure 6:
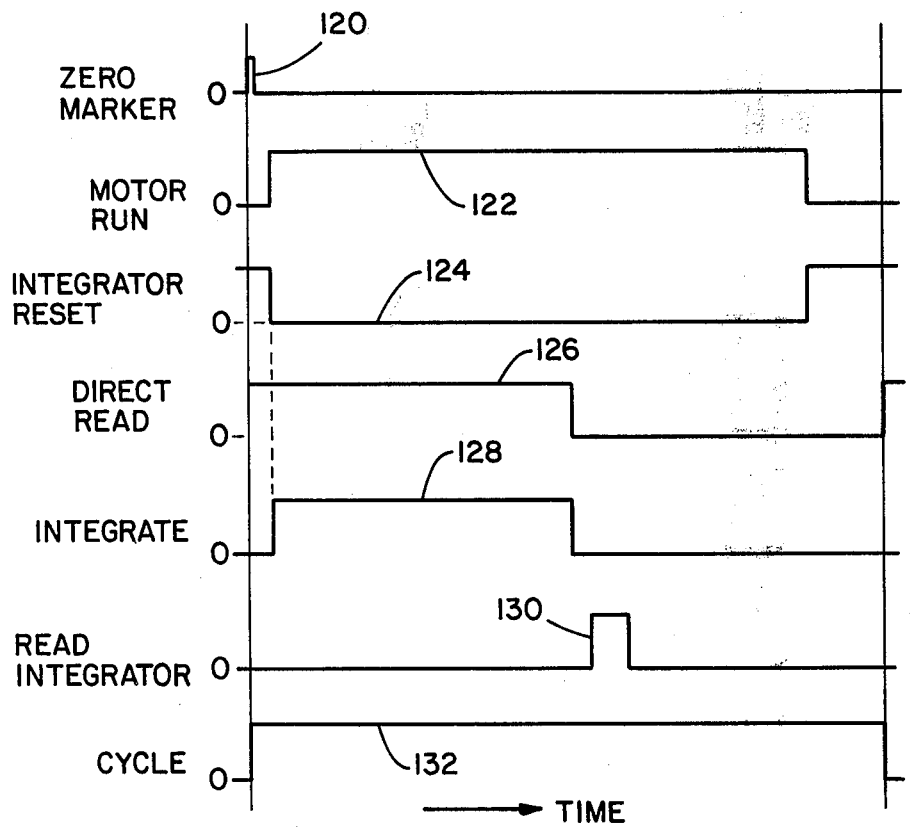
FIG. 6 is a timing diagram useful in understanding the operation of the circuit of FIG. 2.

Referring to FIG. 6, the timing signals for the FIG. 2 circuit are illustrated, which figure in conjunction with FIG. 2, defines the operation of the system. The operation of the zero marker flipflop is indicated by wave form 120, the motor run flipflop by wave form 122 and 124. Flipflop 78, the direct read flipflop, produces wave form 126, while the output from AND gate 90 is illustrated by wave form 128. Wave form 130 indicates the output of the decoder 76 effective for providing the output of the integrator to the chart recorder 16. Wave form 132 is the cycle complete wave form.

Figure 7:
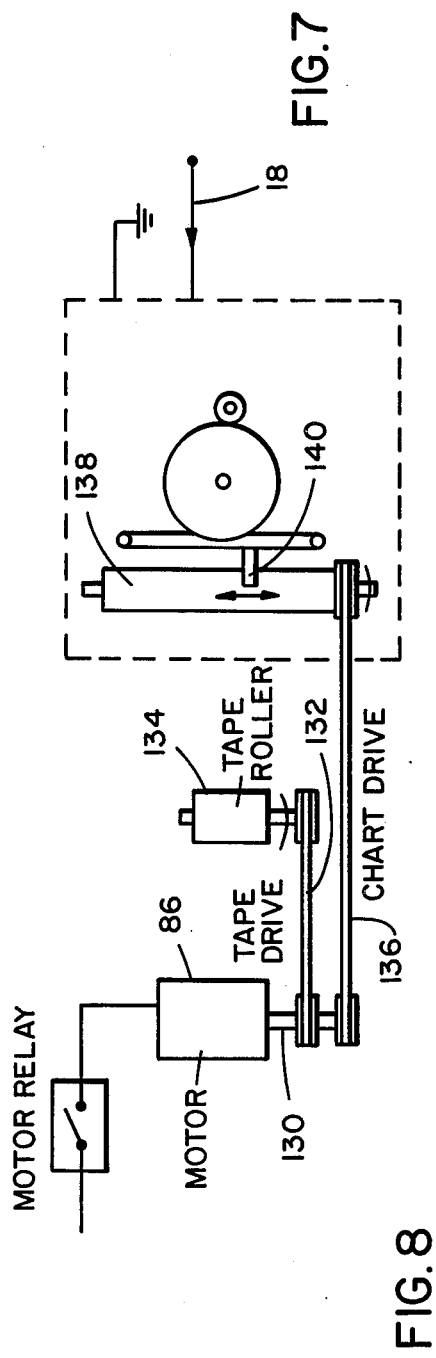
FIG. 7 is a simplified drawing of the mechanical linkage between the drive motor, the tape drive and the recorder chart drive.

Referring to FIG. 7, a schematic of the mechanical drive according to the invention is illustrated. The tape and chart paper recorder are both driven from the motor 86 which has an output shaft 130. From the output shaft the tape drive employs a nonslip belt 132 for driving a roller 134 which feeds the tape past the optics portion of the device. Also deriving its power from shaft 130 is a nonslip belt 136 which is utilized for driving a roll 138 for controlling the passage of chart paper past a recording pen 140. Recording pen 140 is driven in the direction indicated by the arrows by the signal applied to the chart recorder on line 18. This represents the Y coordinate on the graph of FIG. 8. Due to the fact that the tape drive and the recorder drive are connected to the same output shaft 130 there is a definite fixed relationship between movement of the tape and movement of the chart paper. This is highly desirable for the following reasons. When the recorder and tape are driven in a fixed relationship as, for example, a one to one relationship by a synchronous motor, distance along the tape and thus along the chart record corresponds to time of exposure. Events of interest can be related to time of occurrence, an important advantage over prior systems. This also permits the sequencing of the invention by internal timing components.

If the tape during exposure travels at 2 centimeters per hour, 16 centimeters of tape will be exposed during a normal eight hour work shift. When read, the tape and chart can travel at, for example, one centimeter per second. Thus, it will take 16 seconds to read an 8 hour tape.

Referring now to FIG. 8, the output from the chart recorder 16 is illustrated. By coupling the chart recorder with the tape drive the output from the chart recorder can be calibrated in, for example, 8 hour segments to represent a worker's shift. Illustrated in FIG. 8 is a typical wave form for a worker over an eight hour period. The wave form 150 shows a variety of concentration values during his 8 hour shift with three excursions above the 0.10 per million concentration level. At the end of the eight hour shift the recorder pen returns to zero when disconnected from the amplifier 14. Subsequently, when the integrator is connected to the recorder it prints out a bar chart wave form 152 indicative of the integral of the area under the curve 150. This value is the total dose for 8 hours. To obtain the time weighted average exposure it is only necessary to divide the bar chart value by the number of hours of exposure.

While we have shown and described embodiments of this invention in some detail, it will be understood that this description and illustrations are offered merely by way of example, and that the invention is to be limited in scope only by the appended claims.

We claim:

1. A reader recorder device for producing a graph of gas concentration versus time and of total dosage from a portion of gas sensitive tape exposed over a known time period, said device comprising:
    (a) means for reading said gas sensitive tape at a first rate to produce a time varying voltage corresponding to said gas concentration,
    (b) means for linearizing the relationship between gas concentration and said varying voltage.
    (c) integrator means for performing a voltage versus time integration of the linearized voltage to obtain an electrical signal having a magnitude representative of the area under the graph of said time varying voltage over said known time period, said electrical signal representing said total dosage,
    (d) means for recording on chart paper at a second rate said variation in voltage with respect to time and said total dosage, the relationship between the first and second rates permitting a determination of the time of occurrence of a gas concentration change of interest.

2. The device according to claim 1 wherein said first rate and said second rate are equal and the time of occurrence is read directly from said chart paper.

3. The device according to claim 1 wherein said device includes a motor and drive shaft, said shaft driving both said reading means and said recording means thereby to establish the fixed relationship between said first and second rates.

4. The device according to claim 1 wherein said reading means includes:
    (a) a light source,
    (b) a first photocell detector measuring reflected light from said tape to determine gas concentration,
    (c) a reference photocell detector measuring reflected light from an unexposed portion of said tape to regulate the intensity of said light source, and
    (d) a tape drive for transporting said tape past said photocell detectors.

5. The device according to claim 1 wherein said recording means includes:
    (a) a recorder pen vertically displaceable responsive to changes in said voltage, and
    (b) drive means for moving said chart paper past said pen.

6. The device according to claim 4 wherein said recording means includes:
    (a) a recorder pen vertically displaceable responsive to changes in said voltage, and
    (b) drive means for moving said chart paper past said pen.

7. The device according to claim 6 further including a motor and drive shaft from which both said chart drive means and said tape drive are driven.

8. The device according to claim 1 wherein said means for linearizing includes a variable gain amplifier, the output of which is a selectable function of the input.

9. The device according to claim 8 wherein said amplifier includes:

(a) an operational amplifier having a feedback loop, and
(b) a diode network in said feedback loop

* * * * *